(12) United States Patent
Takeshita

(10) Patent No.: US 9,261,450 B2
(45) Date of Patent: Feb. 16, 2016

(54) MICROORGANISM NUMBER-MEASURING APPARATUS

(75) Inventor: Toshiaki Takeshita, Ehime (JP)

(73) Assignee: PANASONIC HEALTHCARE HOLDINGS CO., LTD., Minato-Ku, Tokyo (JP)

(*) Notice: Subject to any disclaimer, the term of this patent is extended or adjusted under 35 U.S.C. 154(b) by 304 days.

(21) Appl. No.: 13/144,319

(22) PCT Filed: Nov. 25, 2010

(86) PCT No.: PCT/JP2010/006867
§ 371 (c)(1),
(2), (4) Date: Jul. 13, 2011

(87) PCT Pub. No.: WO2011/074190
PCT Pub. Date: Jun. 23, 2011

(65) Prior Publication Data
US 2012/0244606 A1    Sep. 27, 2012

(30) Foreign Application Priority Data
Dec. 15, 2009   (JP) ................. 2009-283628

(51) Int. Cl.
| G01N 15/06 | (2006.01) |
| A61B 5/15 | (2006.01) |
| A61B 5/145 | (2006.01) |
| A61B 5/1486 | (2006.01) |
| B01L 3/00 | (2006.01) |
| G01N 33/487 | (2006.01) |
| C12Q 1/00 | (2006.01) |

(52) U.S. Cl.
CPC .......... *G01N 15/0656* (2013.01); *A61B 5/1411* (2013.01); *A61B 5/1486* (2013.01); *A61B 5/14532* (2013.01); *B01L 3/5027* (2013.01); *C12Q 1/006* (2013.01); *G01N 33/48771* (2013.01)

(58) Field of Classification Search
CPC ................ G01N 15/0656; G01N 33/48771; A61B 5/1411; A61B 5/14532; A61B 5/1486; B01L 3/5027; C12Q 1/006
See application file for complete search history.

(56) References Cited

U.S. PATENT DOCUMENTS

| 6,120,676 A * | 9/2000 | Heller et al. ............... 205/777.5 |
| 6,565,509 B1 * | 5/2003 | Say et al. ...................... 600/365 |
| 2005/0284757 A1 | 12/2005 | Allen |

FOREIGN PATENT DOCUMENTS

| JP | 62-139643 A | 6/1987 |
| JP | 2006/023300 A | 1/2006 |
| JP | 2009-214894 A | 9/2009 |
| WO | WO 2009/113250 A1 | 9/2009 |

OTHER PUBLICATIONS

International Search Report for Application No. PCT/JP2010/0006867, Mar. 8, 2011, Panasonic Corporation.

* cited by examiner

*Primary Examiner* — Gautam Prakash
(74) *Attorney, Agent, or Firm* — Shinjyu Global IP

(57) ABSTRACT

A microorganism number-measuring apparatus includes a container holder holding container that accommodates a liquid into which microorganisms are released, power supply unit applying a microorganism-collecting voltage and a microorganism number-measuring voltage to measurement electrode that is dipped in container held by the container holder, and reuse prevention unit that makes measurement electrode burn out after a measurement operation thereof. With this configuration, it is possible to prevent improper reuse of the measurement electrode.

8 Claims, 10 Drawing Sheets

FIG. 11A
FIG. 11B
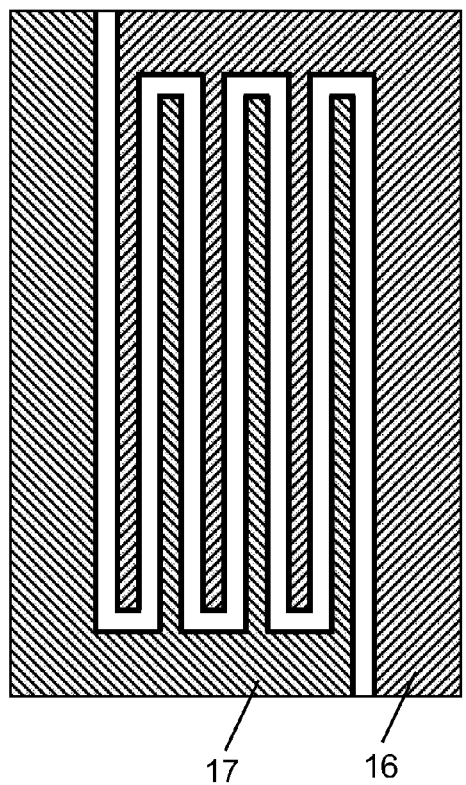
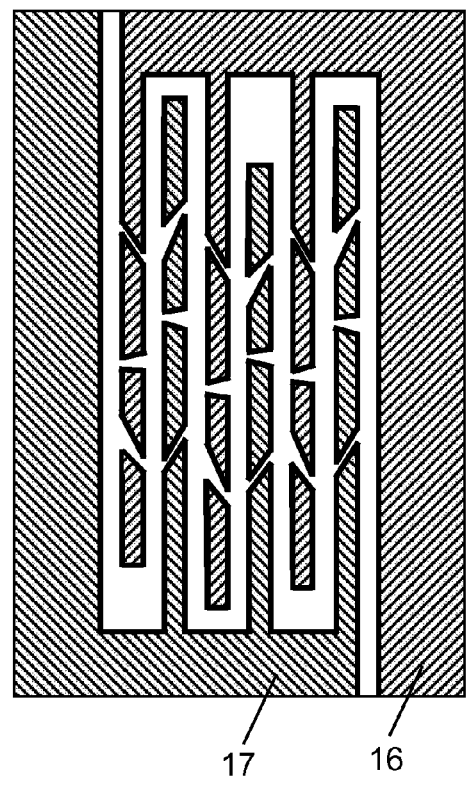

MICROORGANISM NUMBER-MEASURING APPARATUS

THIS APPLICATION IS A U.S. NATIONAL PHASE APPLICATION OF PCT INTERNATIONAL APPLICATION PCT/JP2010/006867.

TECHNICAL FIELD

The present invention relates to a microorganism number-measuring apparatus for measuring, for example, the number of microorganisms (the number of bacteria) present in an oral cavity.

BACKGROUND ART

Measuring cells of conventionally-known microorganism number-measuring apparatuses have a configuration as follows.

The conventional measuring cell includes a container, a measurement space, a liquid containing space, an agitator, and a measurement electrode. A sampling portion disposed at a lower end of a stick-like specimen-sampling carrier is inserted into the container from a top-surface opening of the container The measurement space and the liquid containing space are sequentially disposed upward from the bottom surface of the container. The agitator is disposed on a basal plane of the measurement space. The measurement electrode is disposed above the agitator in the measurement space. The liquid containing space accommodates a liquid (sample liquid).

In addition, a body of the microorganism number-measuring apparatus is disposed outside the measurement space of the container, and includes a driving unit to drive the agitator. The body performs a measurement of the number of microorganisms by using the measuring cell.

When performing the measurement of the number of microorganisms, after the measuring cell is set in the body of the microorganism number-measuring apparatus, the sampling portion of the stick-like specimen-sampling carrier that has collected microorganisms is inserted into the container of the measuring cell from an upper portion thereof. On this occasion, the sampling portion is disposed in the measurement space disposed in a lower portion of the container, together with the liquid accommodated in the liquid containing space of the container. After that, a driving unit disposed below and outside the container drives to rotate the agitator which is disposed on the basal plane of the measurement space. With the rotation of the agitator, the sampling portion is struck to receive impacts, which thereby releases the microorganisms of the sampling portion into the sample liquid.

The released microorganisms are carried to the measurement electrode by an agitated-water flow of the sample liquid agitated by the agitator. Then, the number of the microorganisms is measured at the measurement electrode.

Note that, after finishing the measurement of the number of microorganisms, a user discards the sampling portion and the sample liquid, together with the measuring cell having the measurement electrode (see, for example, Patent Literature 1 listed below).

In this conventional case, the measuring cell having the measurement electrode is discarded after finishing the measurement of the number of microorganisms, and then a fresh measuring cell is used for the next measurement. Accordingly, since a measurement of the number of microorganisms can always be performed by using a fresh measuring cell, the apparatus has been claimed to be a highly reliable and useful device.

On the other hand, however, in the above conventional case, there has been a problem that it is difficult to prevent improper use of measuring cells.

That is, with a measuring cell once used for measuring, the top-surface of the container thereof remains in an open state for easy removal of the used sample liquid from the measuring cell. Hence, there is a possibility for the user to erroneously consider that the measuring cell would be still useable only if the sample liquid is replaced. Based on the consideration, the user would erroneously reuse the used measuring cell, with the sample liquid thereof being replaced.

However, after having been once used for measurement, the measuring cell is in the state where invisibly small microorganisms remain attached to the measurement electrode thereof, even if the sample liquid has been replaced. For this reason, reuse of the measurement electrode once used for measurement will spoil results of the measurement.

CITATION LIST

Patent Literature
Patent Literature 1: Japanese Patent Unexamined Publication No. 2009-214894

SUMMARY OF THE INVENTION

In view of the above mentioned problem, an object of the present invention is to prevent improper use of measurement electrodes.

A microorganism number-measuring apparatus according to the invention includes: a container holder that holds a container accommodating a liquid into which microorganisms are released; a power supply unit that applies a microorganism-collecting voltage and a microorganism number-measuring voltage to a measurement electrode that is dipped into the container held by the container holder; and a reuse prevention unit that makes the measurement electrode burn out after finishing a measuring operation thereof.

Moreover, a microorganism number-measuring apparatus according to the invention includes: a container that accommodates a liquid into which microorganisms are released; a container holder that holds the container; a measurement electrode that is dipped in the container held by the container holder; a power supply unit that applies a microorganism-collecting voltage and a microorganism number-measuring voltage to the measurement electrode; and a reuse prevention unit that makes the measurement electrode burn out after finishing a measuring operation thereof.

That is, in the microorganism number-measuring apparatus according to the invention, the reuse prevention unit is designed to make the used measurement electrode physically burn out after finishing the measuring operation.

Hence, for the next measurement, it is possible to confirm the burnout of the measurement electrode before starting measuring the number of microorganisms, which results in the prevention of reuse of the improper measurement electrode.

BRIEF DESCRIPTION OF DRAWINGS

FIG. 11A is a view illustrating burnout treatment of a comb-like electrode in a microorganism number-measuring apparatus according to a second embodiment of the invention.

FIG. 11B is a view illustrating burnout treatment of the comb-like electrode in the microorganism number-measuring apparatus according to the second embodiment of the invention.

DETAILED DESCRIPTION OF PREFERRED EMBODIMENTS (First Exemplary Embodiment)

Hereinafter, a first embodiment of the present invention will be described with reference to the drawings.

Figure 1:
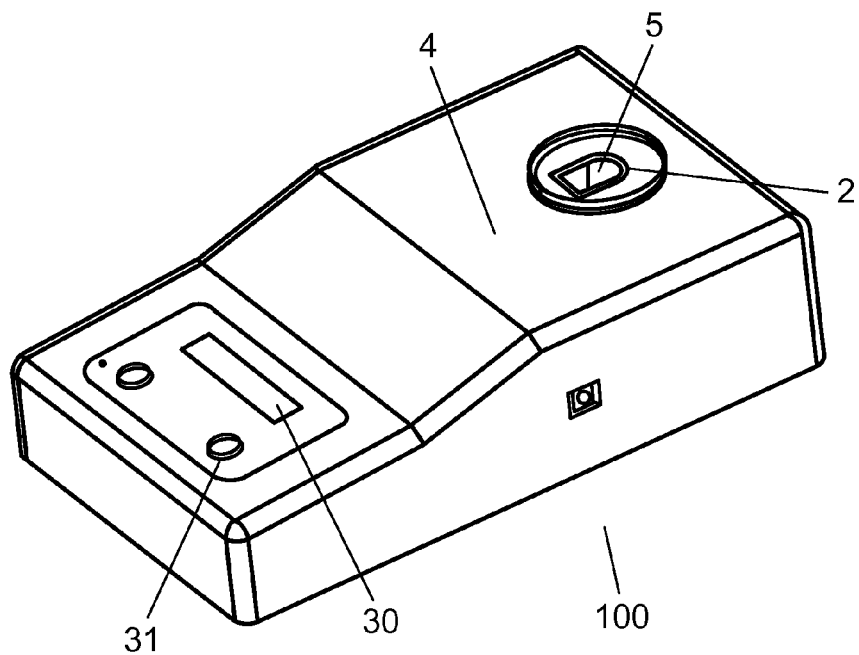
FIG. 1 is a perspective view illustrating a configuration of a microorganism number-measuring apparatus according to a first embodiment of the present invention.
Figure 2:
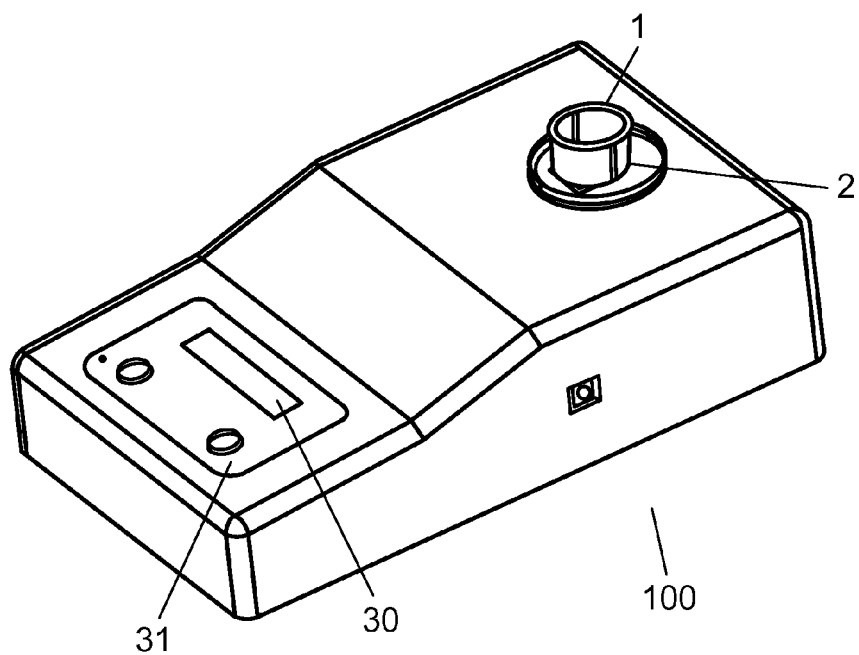
FIG. 2 is a perspective view of the microorganism number-measuring apparatus according to the first embodiment of the invention in a state where a bacteria-measuring cell is loaded therein.
Figure 3:
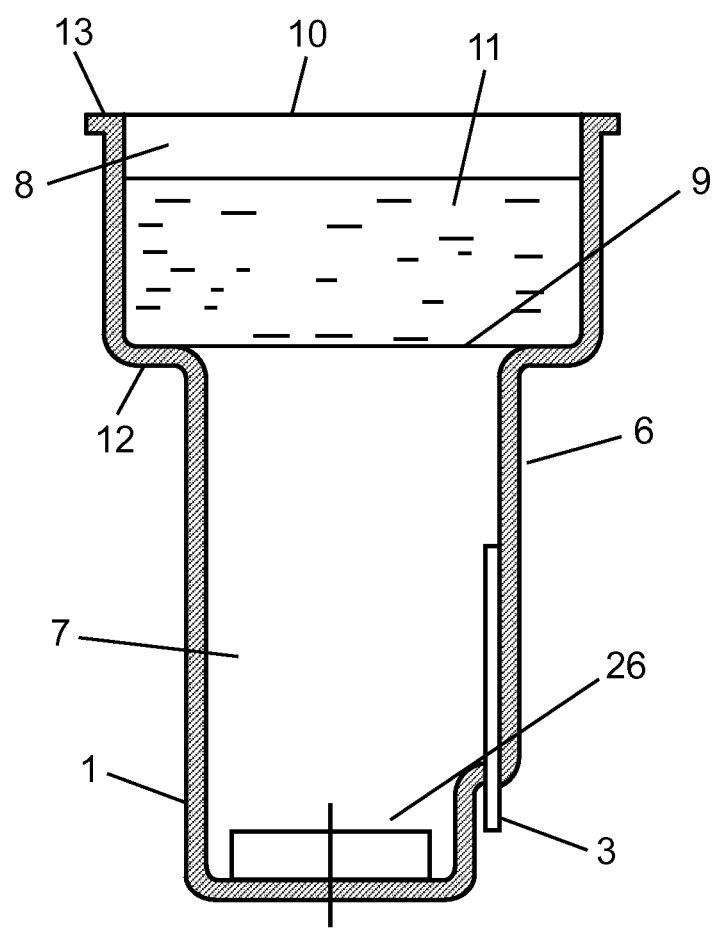
FIG. 3 is a cross-sectional view illustrating a configuration of the bacteria-measuring cell in the microorganism number-measuring apparatus according to the first embodiment of the invention.

FIG. 1 is a perspective view illustrating a configuration of microorganism number-measuring apparatus 100 according to the first embodiment of the invention. FIG. 2 is a perspective view of microorganism number-measuring apparatus 100 according to the first embodiment of the invention in a state where bacteria-measuring cell 1 is loaded therein. And, FIG. 3 is a cross-sectional view illustrating a configuration of bacteria-measuring cell 1 in the microorganism number-measuring apparatus according to the first embodiment of the invention.

Microorganism number-measuring apparatus 100 is a device for measuring the number of microorganisms (the number of bacteria) present in a specimen (saliva, for example) taken from inside an oral cavity. Microorganism number-measuring apparatus 100 includes loading portion (one example of a container holder) 2 at a top-surface thereof at which bacteria-measuring cell 1 is loaded. Moreover, at the inside of microorganism number-measuring apparatus 100, measurement unit 4 (see FIG. 7) is disposed and coupled with measurement electrode 3 of bacteria-measuring cell 1 shown in FIG. 3.

Loading portion 2 has a cylindrical configuration in which the top-surface thereof is opening 5. A lower portion of bacteria-measuring cell 1 is inserted from opening 5 as shown in FIG. 2.

A configuration of bacteria-measuring cell 1 will now be described with reference to FIG. 3.

Bacteria-measuring cell 1 includes container 6, thin film 9, thin film 10, and measurement electrode 3. Container 6 is composed of polycarbonate and has a blind cylinder shape with an open top-surface. Thin film 9 partitions the inside of container 6 into lower measurement space 7 and upper liquid containing space 8. Thin film 10 covers liquid containing space 8 of container 6. Measurement electrode 3 is disposed at a central portion of measurement space 7 in an up-down direction. Moreover, liquid containing space 8 accommodates pure water 11 as a liquid for measurement.

That is, as shown in FIG. 3, measurement space 7 and liquid containing space 8 are sequentially disposed toward an upward direction from the bottom surface of container 6.

Incidentally, thin film 9 and thin film 10 are each composed of a metal foil, specifically an aluminum foil. Thin film 9 is fixed by the outer periphery thereof to stepped portion 12 disposed at a lower portion of liquid containing space 8 of container 6. And, thin film 10 is fixed by the outer periphery thereof to flange 13 disposed at an upper opening of liquid containing space 8 of container 6.

Moreover, measurement electrode 3 is prepared by depositing silver on a PET, i.e. a substrate, by vapor deposition (or depositing palladium by sputtering), and then trimming it by laser processing.

Figure 4:
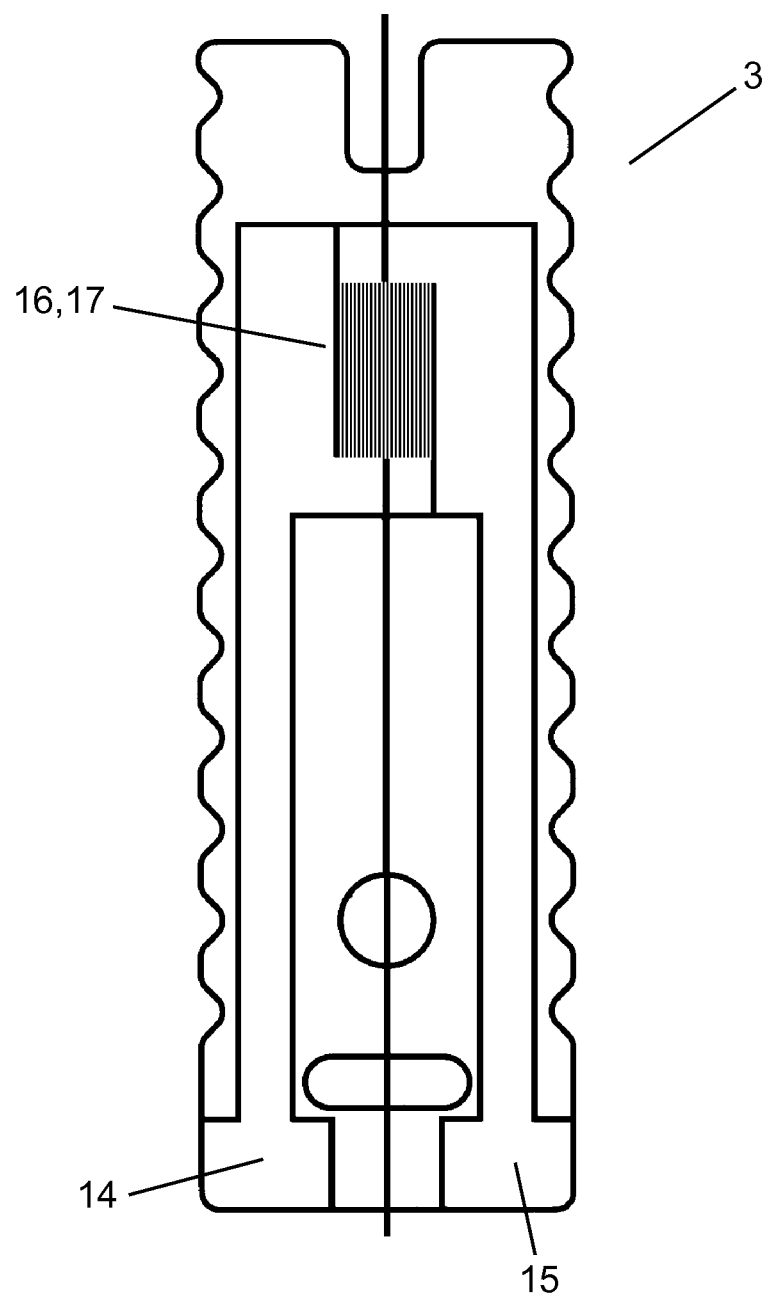
FIG. 4 is a view illustrating a configuration of a measurement electrode in the microorganism number-measuring apparatus according to the first embodiment of the invention.
Figure 5:
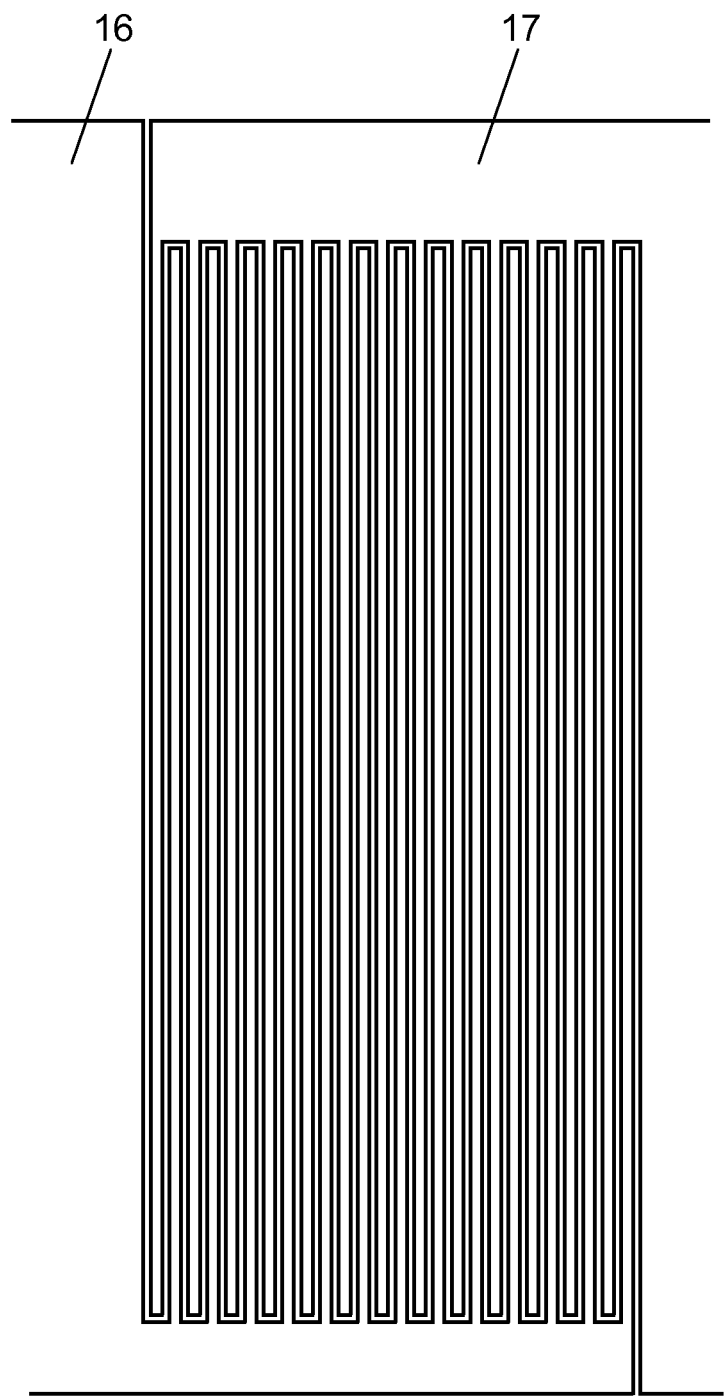
FIG. 5 is a view illustrating the configuration of the measurement electrode in the microorganism number-measuring apparatus according to the first embodiment of the invention.

Next, a configuration of measurement electrode 3 will now be described. FIGS. 4 and 5 are views for illustrating a configuration of measurement electrode 3 in the microorganism number-measuring apparatus according to the first embodiment of the present invention.

As shown in FIG. 4, measurement electrode 3 has a configuration in which comb-like electrodes 16 and 17 are respectively coupled with terminals 14 and 15, in an area between terminals 14 and 15. FIG. 5 shows a configuration of comb-like electrodes 16 and 17.

Comb-like electrodes 16 and 17 are disposed in an opposed state in which both are very close to one another entirely along a long path thereof, thereby generating electrostatic capacity therebetween.

When the number of microorganisms (the number of bacteria) to be detected is large, the electrostatic capacity between comb-like electrodes 16 and 17 becomes large. Therefore, use of the variation in the electrostatic capacity allows the measurement of the number of microorganisms.

Figure 6:
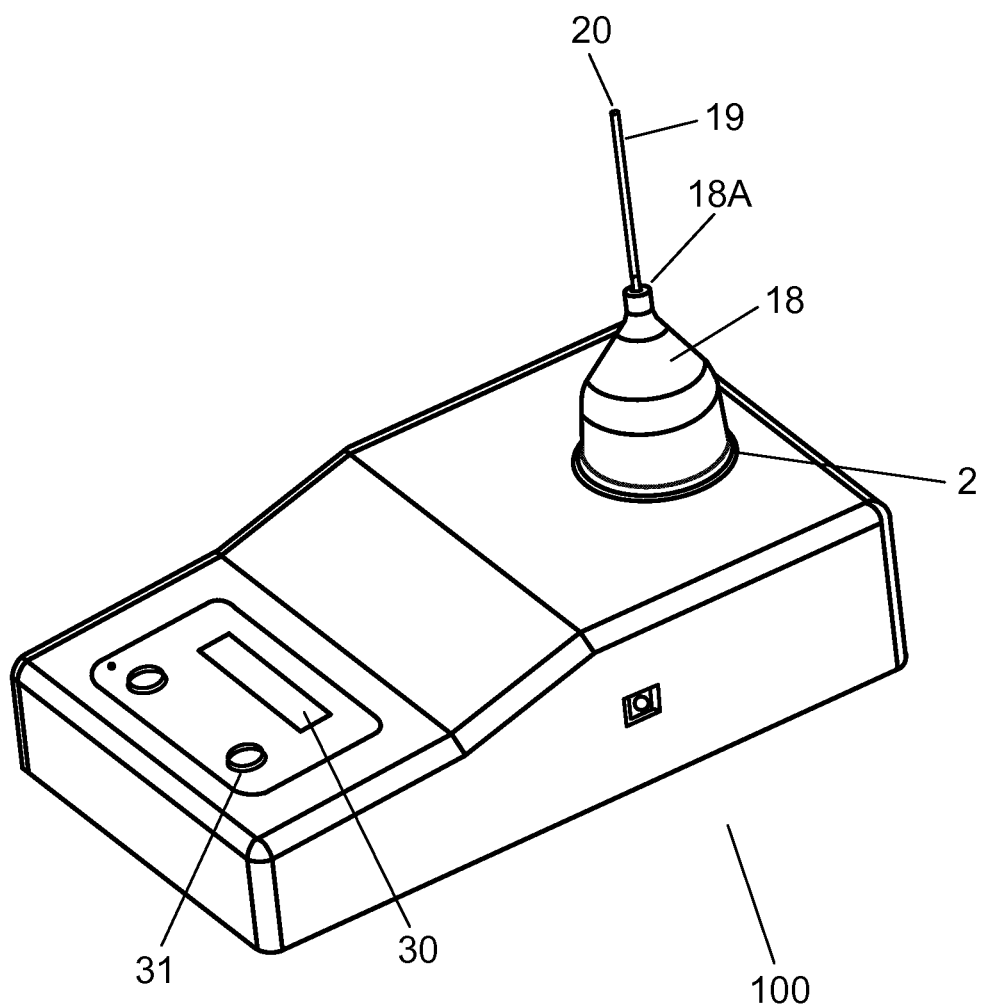
FIG. 6 is a perspective view of the microorganism number-measuring apparatus according to the first embodiment of the invention in a state where a cap, for example, is placed as a container cover of the bacteria-measuring cell, after the bacteria-measuring cell is loaded to the apparatus.

FIG. 6 is a perspective view of microorganism number-measuring apparatus 100 according to the first embodiment of the invention in a state where cap 18, for example, is placed to cover bacteria-measuring cell 1 as a container cover thereof, after bacteria-measuring cell 1 is loaded to the apparatus. As shown in FIG. 6, at a substantially central portion of cap 18, through-hole 18A is disposed, through which stick 20 configuring stick-like specimen-sampling carrier 19 (a cotton swab, for example) penetrates.

Figure 7:
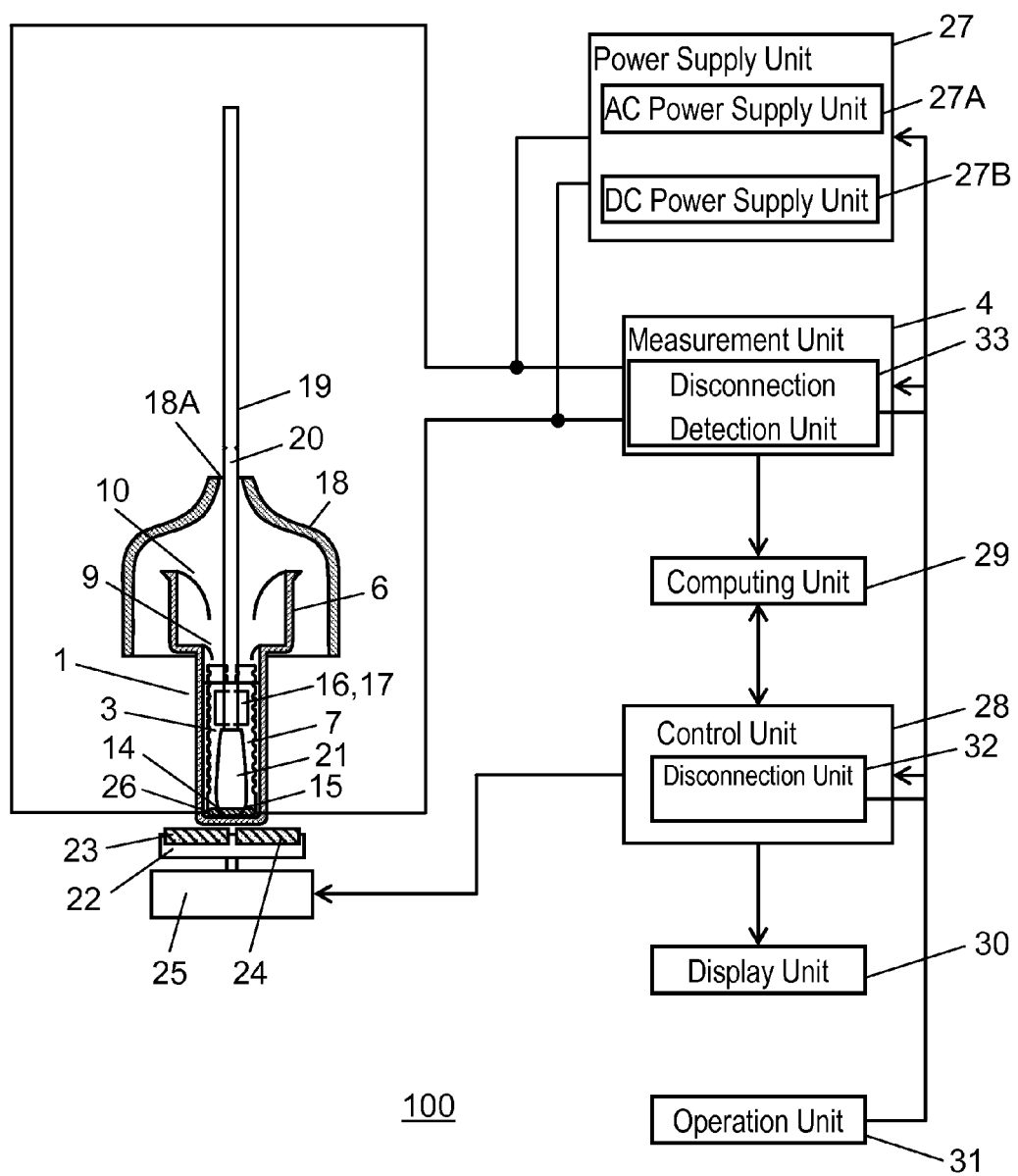
FIG. 7 is a view illustrating a detailed configuration of the microorganism number-measuring apparatus according to the first embodiment of the invention.

Here, a detailed description of the configuration and operation of microorganism number-measuring apparatus 100 will be given. FIG. 7 is a view illustrating the detailed configuration of microorganism number-measuring apparatus 100 according to the first embodiment of the invention.

Specimen-sampling carrier 19 is provided with sampling portion 21 to which cotton is balled up, at a lower end of the carrier as shown in FIG. 7.

Here, how to use microorganism number-measuring apparatus 100 will be described. First, in the embodiment, a user takes stick 20 of specimen-sampling carrier 19 and rubs an inside of the oral cavity of a patient with sampling portion 21. In this way, the user is able to collect microorganisms (bacteria) together with saliva by using sampling portion 21.

Next, an upper end (an end at which sampling portion 21 is not disposed) of specimen-sampling carrier 19 is placed at a central portion of thin film 10 of bacteria-measuring cell 1 shown in FIG. 3, and then pushed straight down. In this way, the upper end of specimen-sampling carrier 19 pierces a hole in thin film 10 and a hole in thin film 9 subsequently.

With this state, the user enlarges the holes pierced in thin film 10 and thin film 9, by rotationally moving stick 20 of specimen-sampling carrier 19 in a concentric manner. This causes pure water 11 held in liquid containing space 8 to flow into measurement space 7, resulting in a submergence of measurement electrode 3 below the water surface of pure water 11.

Next, the user once pulls out specimen-sampling carrier 19 from bacteria-measuring cell 1. Then, the user inserts specimen-sampling carrier 19 into measurement space 7 of bacteria-measuring cell 1, with sampling portion 21 being downward, as shown in FIG. 7. And then, the user places cap 18 to cover container 6 such that an upper end of stick 20 of specimen-sampling carrier 19 penetrates through through-hole 18A of cap 18, as shown in FIGS. 6 and 7. As a result, sampling portion 21 is disposed below the water surface of pure water 11 in measurement space 7 so as to be in a submerged state.

In this state, at a location over container 6 of bacteria-measuring cell 1, through-hole 18A of cap 18 serves as a supporting portion to movably support an upper portion of stick 20 of specimen-sampling carrier 19. Sampling portion 21 and a portion of stick 20 located below the supporting portion are able to rotate in a horizontal direction, with the supporting portion being used as a loose rotational axis.

FIG. 7 shows an electrical block diagram as well, of microorganism number-measuring apparatus 100. Rotor 22 is disposed beneath the bottom of container 6. Magnets 23 and 24 are disposed at rotor 22.

Consequently, when motor 25, i.e., a driving unit, rotates rotor 22 with magnets 23 and 24, the rotating magnets entail a rotation of stick-like agitator 26 that is movably disposed at the inside bottom of container 6. By rotating, agitator 26 strikes sampling portion 21 of specimen-sampling carrier 19.

As a result, sampling portion 21 is subjected to impacts in a flapping manner, which allows the oral-cavity microorganisms collected in sampling portion 21 to be effectively released into pure water 11.

Moreover, stick 20 moves in a conical manner such that through-hole 18A supporting stick 20 is used as a tip of the cone. Therefore, in measurement space 7, not only the rotational force of sampling portion 21 but also the rotational force of stick 20 adjacent to sampling portion 21 works as a force to agitate pure water 11. As a result, pure water 11 in measurement space 7 is subjected to the agitating action large enough to effectively reach comb-like electrodes 16 and 17 located above.

Then, after finishing the release operation described above, a detection of the microorganisms by using comb-like electrodes 16 and 17 is started.

Regarding the measurement of microorganisms, a further description will be given with reference to FIG. 7. In order to collect microorganisms released into pure water 11, alternating-current power supply unit 27A of power supply unit 27 applies an alternating voltage (a microorganism-collecting voltage) for collecting bacteria to terminals 14 and 15 (see FIG. 4) of measurement electrode 3. Thereby, the microorganisms in pure water 11 are polarized to positive and negative states by a dielectrophoretic force caused by the applied voltage. As a result, the microorganisms are attracted to a portion of comb-like electrodes 16 and 17 shown in FIG. 5. In this process, the electrostatic capacity becomes large with increasing number of the microorganisms (bacteria) collected between comb-like electrodes 16 and 17.

Measurement unit 4 measures a magnitude of the electrostatic capacity in accordance with an instruction from control unit 28, and sends the result thereof to computing unit 29. Computing unit 29 determines a rate of change in the electrostatic capacity based on the measurement result of measurement unit 4, converts the rate into the number of the microorganisms (bacteria) by the same procedure as conventional one, and then displays the result thereof on display unit 30 via control unit 28.

Incidentally, operation unit 31 shown in FIG. 7 is one for the user to input instructions for a sequence of operations described above.

In microorganism number-measuring apparatus 100 according to the embodiment, disconnection unit 32 is disposed inside the control unit 28 as a reuse prevention unit for bacteria-measuring cell 1 which has been used for a measurement, as shown in FIG. 7. Disconnection unit 32 makes measurement electrode 3 physically burn out after finishing measuring microorganisms. Therefore, for the next measurement, it is possible that disconnection detecting unit 33 disposed inside measurement unit 4 confirms the burnout of measurement electrode 3 before starting measuring the bacteria.

Hence, in case a user tries to reuse bacteria-measuring cell 1 (reuse of measurement electrode 3), it is possible to prompt the user to use another fresh bacteria-measuring cell 1 (use of fresh measurement electrode 3).

As a result, by using microorganism number-measuring apparatus 100 according to the embodiment, it is possible to prevent improper reuse of bacteria-measuring cell 1 (improper reuse of measurement electrode 3).

Hereinafter, a detailed description will be given regarding the prevention of improper reuse of bacteria-measuring cell 1.

In bacteria-measuring cell 1 which has been used for measuring bacteria, the top surface of container 6 thereof is in the open state for easy removal of used pure water 11 from bacteria-measuring cell 1. Hence, there is a possibility for a user to erroneously consider that bacteria-measuring cell 1 would be still useable only if the sample liquid is replaced. Based on the erroneous consideration, the user would replace pure water 11 in bacteria-measuring cell 1 and use the cell again.

However, after having been once used for a measurement, used bacteria-measuring cell 1 is in the state where some of invisibly small microorganisms present during the measurement still remain inside container 6 and on measurement electrode 3, even if pure water 11 thereof is replaced. For this reason, reuse of bacteria-measuring cell 1 once used for a measurement makes it impossible to perform a proper measurement.

Moreover, comb-like electrodes 16 and 17 of bacteria-measuring cell 1 are made of silver. Therefore, after used pure water 11 is removed from bacteria-measuring cell 1, microscopic organic materials in the air will adhere to comb-like electrodes 16 and 17, which makes it impossible to perform a proper measurement. For this reason as well, reuse of bacteria-measuring cell 1 (measurement electrode 3) once used for a measurement spoils proper results from the measurement.

In contrast, in microorganism number-measuring apparatus 100 according to the embodiment, disconnection unit 32, i.e., the reuse prevention unit, is disposed so as to treat used bacteria-measuring cell 1 such that measurement electrode 3 thereof is made to physically burns out after finishing measurement operation. Therefore, improper reuse of bacteria-measuring cell 1 can be prevented.

Next, an operation of microorganism number-measuring apparatus 100 according to the first embodiment of the present invention will be described with reference to a flowchart.

Figure 8:
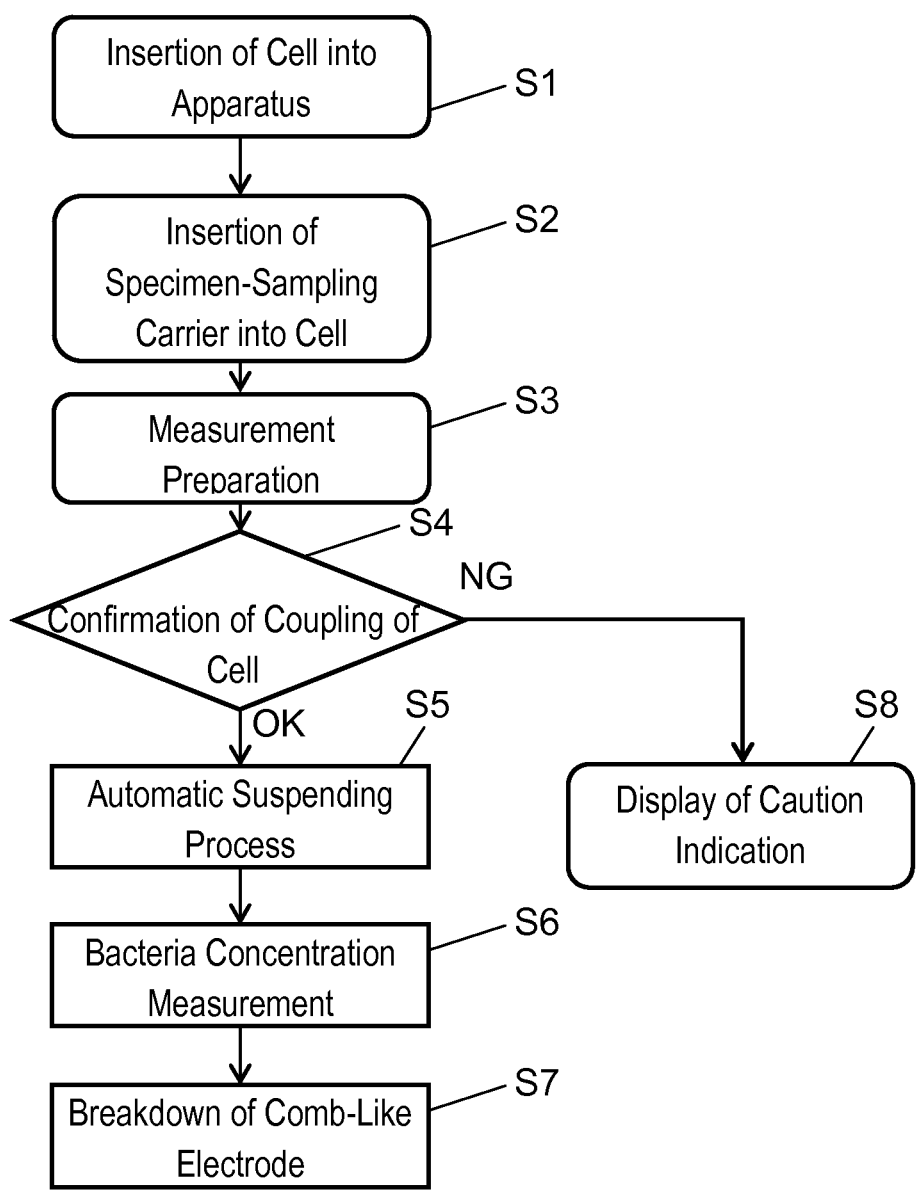
FIG. 8 is a flowchart illustrating an operation of the microorganism number-measuring apparatus according to the first embodiment of the invention.

FIG. 8 is the flowchart illustrating the operation of microorganism number-measuring apparatus 100 according to the first embodiment of the invention.

First, a user inserts fresh bacteria-measuring cell 1 into loading portion 2 of microorganism number-measuring apparatus 100, as shown in FIG. 2 (Step S1).

Next, the user inserts sampling portion 21 of specimen-sampling carrier 19 into measurement space 7 disposed in bacteria-measuring cell 1, as shown in FIG. 7 (Step S2).

Then, the user operates operation unit 31 shown in FIG. 2 to start a preparation for measurement (Step S3). After starting the preparation for measurement, control unit 28 confirms coupling of bacteria-measuring cell 1, and disconnection detecting unit 33 confirms a state of comb-like electrodes 16 and 17 of measurement electrode 3 (Step S4). Specifically, control unit 28 starts by causing motor 25 (one example of a driving unit to rotate pure water 11) to rotate at a speed of 1200 rpm.

Thereby, stick-like agitator 26 disposed at the inside bottom of cylindrical container 6 is rotated to agitate pure water 11. Pure water 11 is rotated around a center axis in an up-down direction, which generates an agitated-water stream in a spiral state (a water stream rotating inside container 6). In addition, agitator 26 strikes sampling portion 21 of specimen-sampling carrier 19, thereby causing microorganisms of sampling portion 21 to be released into pure water 11. After that, the microorganisms are carried to comb-like electrodes 16 and 17 by the agitated-water stream of pure water 11.

In this process, in accordance with an instruction from disconnection detection unit 33 disposed in measurement unit 4, alternating-current power supply unit 27A applies an alternating-current voltage of 800 kHz and 1V to comb-like electrodes 16 and 17. If comb-like electrodes 16 and 17 are in a proper state, electric current flows between comb-like electrodes 16 and 17, with the microorganisms being used as a medium which have been carried to comb-like electrodes 16 and 17.

On the other hand, if comb-like electrodes 16 and 17 have burned out by means of disconnection unit 32, no electric current flows between comb-like electrodes 16 and 17. Therefore, by detecting the state of the electric current, disconnection detecting unit 33 is able to detect whether or not comb-like electrodes 16 and 17 have burned out.

When fresh bacteria-measuring cell 1 is used, disconnection detecting unit 33 judges that comb-like electrodes 16 and 17 are in a proper state without burnout, thus the confirmation of coupling of the cell is completed.

In the case where bacteria-measuring cell 1 is judged to be in a proper state, automatic suspending process is started (Step S5). Specifically, control unit 28 causes motor 25 to rotate at a speed of 3000 rpm, which thereby releases remaining microorganisms from sampling portion 21 into pure water 11. Note that the automatic suspending process is carried out for, for example, one minute.

Next, a measurement of the number of microorganisms (the number of bacteria) is performed (Step S6). Specifically, control unit 28 changes the speed of rotation of motor 25 from 3000 rpm to 1200 rpm that is suitable for collecting bacteria. In the embodiment, during the measurement of the number of microorganisms, the speed of rotation of rotor 22 is reduced so that the microorganisms collected to comb-like electrodes 16 and 17 will not be detached from comb-like electrodes 16 and 17 due to the agitated-water stream.

Then, control unit 28 instructs alternating-current power supply unit 27A of power supply unit 27 to apply both a bacteria-collecting voltage (microorganism-collecting voltage) of 3 MHz, 10V and a measuring voltage (microorganism number-measuring voltage) of 800 kHz, 1V to comb-like electrodes 16 and 17, simultaneously for 20 seconds. And then, measurement unit 4 measures the magnitude of the electrostatic capacity, and sends the result thereof to computing unit 29. Computing unit 29 determines a rate of change in the electrostatic capacity, converts the rate into the number of microorganisms (the number of bacteria) by the same procedure as conventional one, and then displays the result thereof on display unit 30 via control unit 28. Thus, the measurement is completed.

Next, in order to prevent improper use of used bacteria-measuring cell 1, comb-like electrodes 16 and 17 of measurement electrode 3 are made to burn out (Step S7). Specifically, for comb-like electrodes 16 and 17, disconnection unit 32 switches over the connection from alternating-current power supply unit 27A to direct-current power supply unit 27B. Then, direct-current power supply unit 27B applies a direct current voltage of 5V for 10 seconds, as a disconnection voltage.

In this way, comb-like electrodes 16 and 17 burn out, and after that it is impossible for bacteria-measuring cell 1 to be reused. Regarding the burnout treatment, a more detailed description will be given later.

In the case where the user tries to reuse bacteria-measuring cell 1 whose comb-like electrodes 16 and 17 have burned out, the operation proceeds again in sequence of steps S1, S2, and S3 shown in FIG. 8. However, in step S4, because of comb-like electrodes 16 and 17 having burned out, no electric current flows between comb-like electrodes 16 and 17. Then, disconnection detecting unit 33 of measurement unit 4 detects the state of electric current, and measurement unit 4 thereby judges that comb-like electrodes 16 and 17 are not in a proper state. Then, control unit 28 displays on display unit 30 a notice of caution for use of fresh bacteria-measuring cell 1, reading "Use Fresh Bacteria-Measuring Cell 1," for example. After that, the successive treatments are halted (Step S8).

As a result, it is possible to prevent reuse of bacteria-measuring cell 1 (measurement electrode 3) which has been once used, and therefore prevent improper use of bacteria-measuring cell 1 (measurement electrode 3).

Figure 9A:
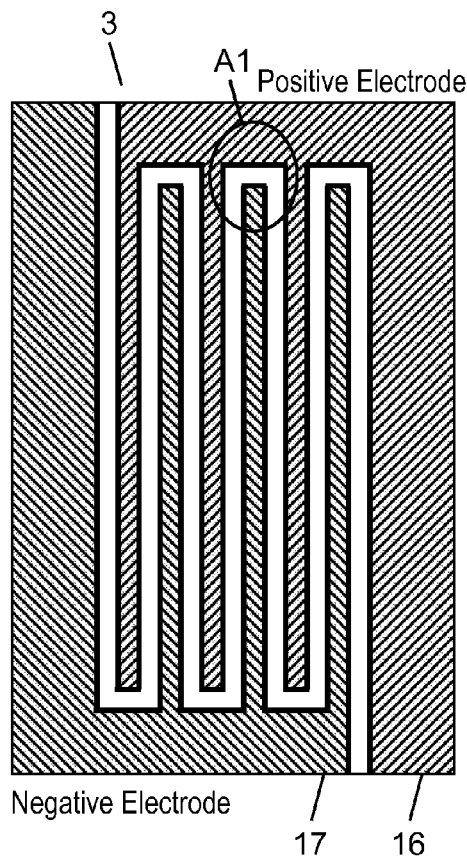
FIG. 9A is a view illustrating burnout treatment of a comb-like electrode in the microorganism number-measuring apparatus according to the first embodiment of the invention.
Figure 9B:
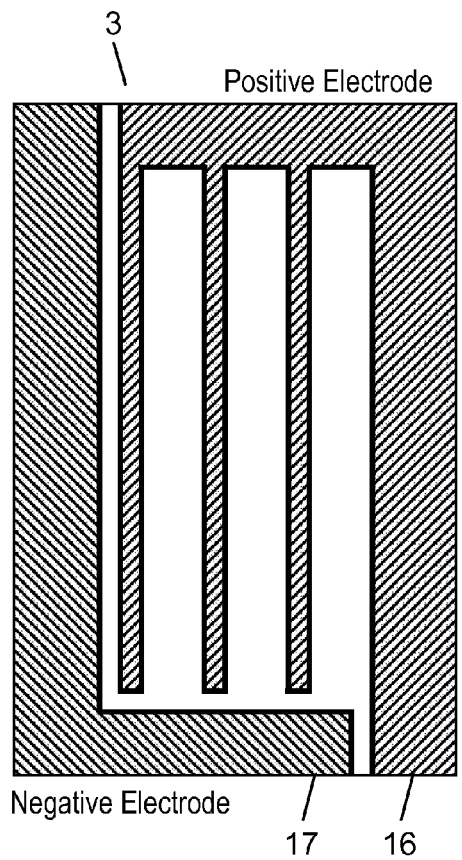
FIG. 9B is a view illustrating burnout treatment of the comb-like electrode in the microorganism number-measuring apparatus according to the first embodiment of the invention.
Figure 10:
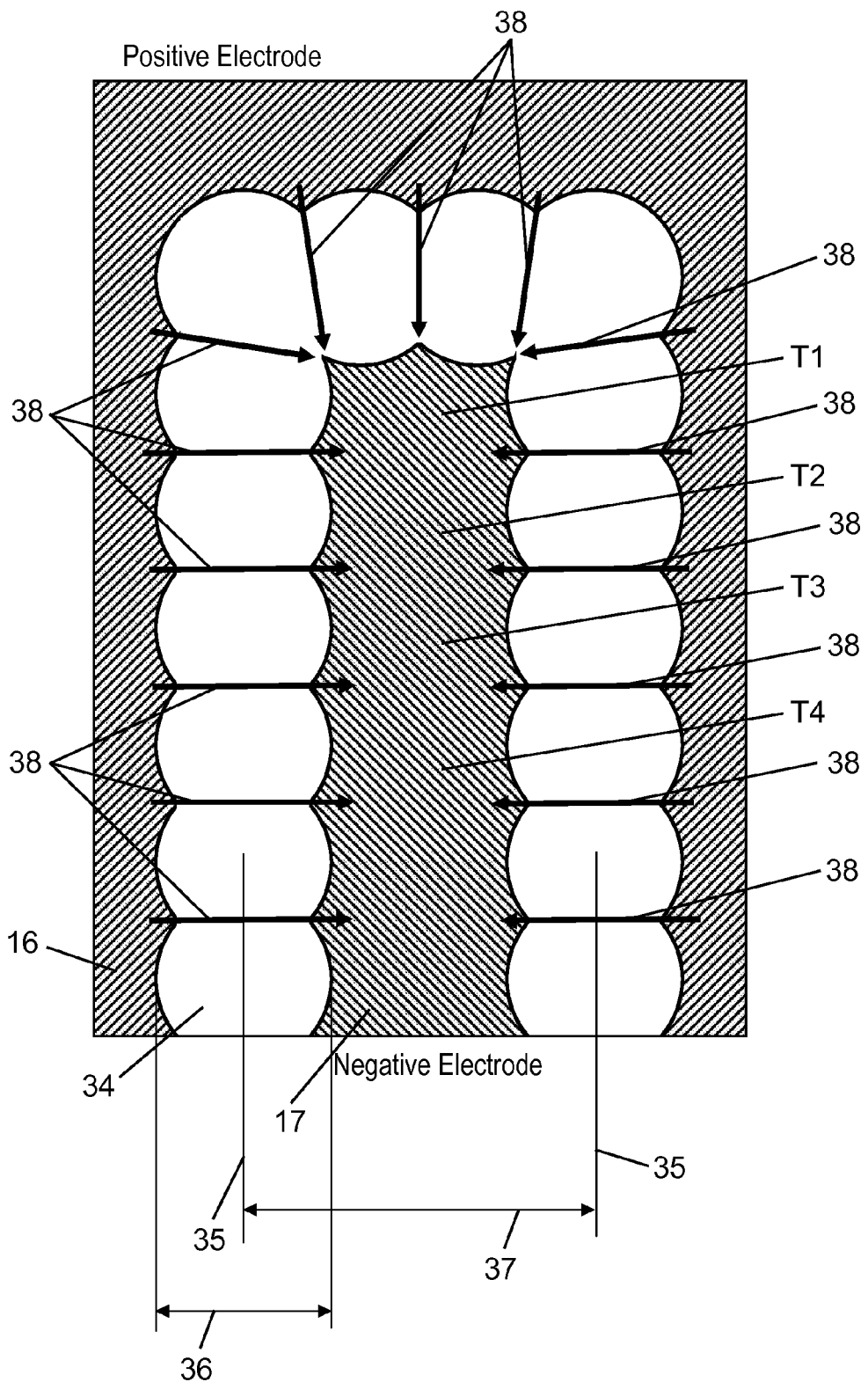
FIG. 10 is a view illustrating burnout treatment of the comb-like electrode in the microorganism number-measuring apparatus according to the first embodiment of the invention.

Here, the burnout treatment of comb-like electrodes 16 and 17 will be described in detail with reference to the drawings. FIGS. 9A, 9B, and 10 are views for illustrating the burnout treatment of comb-like electrodes 16 and 17 in the microorganism number-measuring apparatus according to the first embodiment of the invention. Note that FIGS. 9A and 9B are simplified views, for explanation, of measurement electrode 3 shown in FIG. 5. FIG. 10 is a magnified view of portion A1 of FIG. 9.

Measurement electrode 3 shown in FIG. 9A is prepared by depositing silver on PET, i.e., a substrate, by vapor deposition, and then trimming it to form comb-like electrodes 16 and 17 with a laser having a spot diameter of 25 µm. Therefore, in comb-like electrodes 16 and 17, as shown in FIG. 10, interelectrode groove 34 between the electrodes is configured such that circles are sequentially connected one another with a partial overlap to form a continuous shape. Hence, comb-like electrodes 16 and 17 have undulating sides which are disposed opposite to one another and symmetric with respect to center line 35 that connects centers of the consecutive circles.

Incidentally, in the embodiment, since the spot diameter of the laser is set to 25 μm, then gap width 36 between comb-like electrodes 16 and 17 is 25 μm. And, in the example of FIG. 10, pitch 37 between comb-like electrodes 16 and 17 is set to 50 μm.

Starting with the normal state shown in FIG. 9A, when comb-like electrodes 16 and 17 are made to burn out, disconnection unit 32 switches over the power supply unit from alternating-current power supply unit 27A to direct-current power supply unit 27B, and couples the power supply unit with terminals 14 and 15 of measurement electrode 3. Thereby, a direct-current voltage of 5 V is applied to comb-like electrodes 16 and 17 coupled with terminals 14 and 15, with comb-like electrode 16 being positive and comb-like electrode 17 being negative.

This leads to a concentrated electric current flow across portion 38 at which comb-like electrodes 16 and 17 are located closest one another as shown in FIG. 10. For this reason, heat is generated at negative-side comb-like electrode 17 to which the electric current concentrates, thereby causing the silver of comb-like electrode 17 to peel off from the PET.

Incidentally, the peel-off starts from an edge portion of negative-side comb-like electrode 17. First, once edge portion T1 is lifted from the PET due to the heat, the agitated-water stream (the water stream rotating inside container 6) of pure water 11 peels and tears off edge portion T1. Next, when edge portion T2 is lifted from the PET, the water stream peels and tears off edge portion T2. In this manner, such peeling gradually proceeds to edge portions T3, T4, and so on. Finally, negative-side comb-like electrode 17 becomes in a state of a complete burnout (burned down) as shown in FIG. 9B. As a result, it is possible to make measurement electrode 3 burn out.

Note that the time period for applying the direct-current voltage by direct-current power supply unit 27B is set to one during which negative-side comb-like electrode 17 burns out completely. The time period varies depending on solution electric conductivity of pure water 11. The solution electric conductivity varies depending on the quality and quantity of saliva of the patient, which is collected together with the microorganisms when rubbing the inside of the oral cavity of the patient with sampling portion 21 for collecting the microorganisms. Also, the solution electric conductivity varies depending on the quality and quantity of adhesive which bonds sampling portion 21 to stick 20 of specimen-sampling carrier 19. That is, these adhesive and saliva of the patient are eluted into pure water 11 together with the microorganisms from sampling portion 21, which causes variations in the solution electric conductivity of pure water 11.

Regarding conditions for a complete burnout of negative-side comb-like electrode 17, when the solution electric conductivity is high, the direct-current voltage becomes low and the time period thereof becomes short because of ease of electric current flow. In contrast, when the solution electric conductivity is low, the direct-current voltage becomes high and the time period thereof becomes long. In the embodiment, in order to make measurement electrode 3 burn out completely even if the solution electric conductivity is low, the applied voltage is set to 5V and the time period thereof is set to 10 seconds.

Note that, during burning out of measurement electrode 3, the agitated-water stream plays a role in aiding comb-like electrode 17 in peeling off, as described above. Moreover, after peeling-off of comb-like electrode 17, the agitated-water stream rapidly quenches heat of comb-like electrode 17, which allows the burnout of measurement electrode 3 with an appropriate environment for burnout being kept.

As a result, it is possible to prevent reuse of bacteria-measuring cell 1 (measurement electrode 3) which has been once used, and therefore prevent improper use of bacteria-measuring cell 1 (measurement electrode 3).

Furthermore, during burning out of measurement electrode 3, negative-side comb-like electrode 17 is in a state of a complete burnout as shown in FIG. 9B, which allows visual confirmation of bacteria-measuring cell 1 (measurement electrode 3) having burned out. Hence, the user is able to recognize such as "this is a used measurement electrode". From this viewpoint, it is possible to prevent improper use of bacteria-measuring cell 1 (measurement electrode 3).

(Second Exemplary Embodiment)

As described above, in the first embodiment, for preventing reuse of measurement electrode 3, microorganism number-measuring apparatus 100 performs the following operations after finishing measuring the number of microorganisms. That is, disconnection unit 32 switches over the power supply unit from alternating-current power supply unit 27A to direct-current power supply unit 27B, and couples the power supply unit with terminals 14 and 15 of measurement electrode 3. Thereby, a direct-current voltage of 5 V is applied such that comb-like electrode 16 is positive and comb-like electrode 17 is negative.

In contrast, in the second embodiment, for preventing reuse of measurement electrode 3, an alternating-current voltage is applied to comb-like electrodes 16 and 17 as a burnout voltage from alternating-current power supply unit 27A without using direct-current power supply unit 27B, in accordance with an instruction from disconnection unit 32.

Specifically, alternating-current power supply unit 27A applies an alternating-current voltage (10 Hz, 10 V), for 10 seconds, to comb-like electrodes 16 and 17 of measurement electrode 3.

That is, in the embodiment, a reuse prevention unit causes alternating-current power supply unit 27A of power supply unit 27 to apply the alternating-current voltage, as a burnout alternating-current voltage, between comb-like electrodes 16 and 17 of measurement electrode 3. The applied alternating-current voltage has a frequency lower than those of a microorganism-collecting voltage (3 MHz, 10 V) and a microorganism number-measuring voltage (800 kHz, 1 V).

FIGS. 11A and 11B are views illustrating burnout treatment of comb-like electrodes 16 and 17 in a microorganism number-measuring apparatus according to the second embodiment of the invention. FIG. 11A shows a state before the burnout alternating-current voltage (10 Hz, 10 V) described above is applied for 10 seconds between comb-like electrodes 16 and 17 in order to prevent reuse of measurement electrode 3. FIG. 11B shows a state after the burnout alternating-current voltage (10 Hz, 10 V) described above is applied for 10 seconds between comb-like electrodes 16 and 17 in order to prevent reuse of measurement electrode 3.

In the embodiment, as shown in FIG. 11B, comb-like electrodes 16 and 17 are in a state where both electrodes have largely burned out to blisteringly segmented. That is, in this embodiment both comb-like electrodes 16 and 17 burn largely out, while in the first embodiment negative-side comb-like electrode 17 burns out by applying direct-current voltage.

In accordance with the embodiment, in the configuration of microorganism number-measuring apparatus 100 shown in FIG. 7, it is possible to simplify the configuration of power supply unit 27 by eliminating the need for direct-current power supply unit 27B through means that alternating-current power supply unit 27A applies the burnout alternating-current voltage (10 Hz, 10 V) for 10 seconds.

Note that, in the embodiment, regarding the burnout alternating-current voltage (one example, 10 Hz, 10 V) applied between comb-like electrodes 16 and 17 from alternating-current power supply unit 27A, it is intended to use an alternating-current voltage with a frequency lower than commercial frequencies (50 Hz or 60 Hz, in most countries in the world including Japan).

Moreover, in the embodiment as well, it is after finishing measuring the number of microorganisms (the number of bacteria) that comb-like electrodes 16 and 17 are made to burn out by applying the burnout alternating-current voltage (10 Hz, 10 V) between comb-like electrodes 16 and 17 from alternating-current power supply unit 27A.

Furthermore, in the embodiment as well, before measurement operation of measurement electrode 3, the burnout detection of measurement electrode 3 is performed.

Specifically, in a similar way to the first embodiment, in accordance with an instruction from disconnection detection unit 33 disposed in measurement unit 4, an alternating-current voltage of 800 kHz and 1V (identical to the microorganism number-measuring voltage) is applied to comb-like electrodes 16 and 17 from alternating-current power supply unit 27A. Then, if comb-like electrodes 16 and 17 are in a proper state, electric current flows between comb-like electrodes 16 and 17, with the microorganisms (bacteria) being used as a medium, which have been carried to comb-like electrodes 16 and 17.

On the other hand, if comb-like electrodes 16 and 17 have burned out in accordance with an instruction from disconnection unit 32, no electric current flows between comb-like electrodes 16 and 17. Therefore, by detecting the state of the electric current, disconnection detecting unit 33 is able to detect whether or not comb-like electrodes 16 and 17 have burned out.

Note that, in the embodiment, the alternating-current voltage applied to measurement electrode 3 for performing burnout detection is one that has a frequency higher than that of the burnout alternating-current voltage (10 Hz, 10 V). Specifically, the burnout detection is configured so as to be performed by applying the microorganism number-measuring voltage (800 kHz, 1 V) to measurement electrode 3.

As described in the embodiment, during burning out of measurement electrode 3, comb-like electrodes 16 and 17 become in a state where both have largely burned out as shown in FIG. 11B. Therefore, the user is able to visually confirm that bacteria-measuring cell 1 (measurement electrode 3) has burned out. Hence, the user is able to recognize that this is a used measurement electrode. From this viewpoint, it is possible to prevent improper use of bacteria-measuring cell 1 (measurement electrode 3).

INDUSTRIAL APPLICABILITY

As described above, the present invention is useful for, for example, microorganism number-measuring apparatuses for measuring the number of microorganisms (the number of bacteria) present in an oral cavity, because the invention provides them with the capability of preventing improper use of measurement electrodes thereof.

REFERENCE MARKS IN THE DRAWINGS 1 bacteria-measuring cell
2 loading portion (container holder)
3 measurement electrode
4 measurement unit
5 opening
6 container
7 measurement space
8 liquid containing space
9 thin film
10 thin film
11 pure water
12 stepped portion
13 flange
14, 15 terminal
16, 17 comb-like electrode
18 cap
18A through-hole
19 specimen-sampling carrier
20 stick
21 sampling portion
22 rotor
23, 24 magnet
25 motor
26 agitator
27 power supply unit
27A alternating-current power supply unit
27B direct-current power supply unit
28 control unit
29 computing unit
30 display unit
31 operation unit
32 disconnection unit (reuse prevention unit)
33 disconnection detection unit
34 interelectrode groove
35 center line
36 gap width
37 pitch
38 portion at which electrodes are located closest one another
100 microorganism number-measuring apparatus

The invention claimed is:

1. A microorganism number-measuring apparatus comprising:
a container accommodating a first liquid into which microorganisms are released;
a measurement electrode formed on a substrate and immersed in the first liquid, the measurement electrode including a pair of comb-like electrodes;
a power supply connected to the pair of comb-like electrodes on the substrate of the measurement electrode in the first liquid and applying a microorganism collecting AC voltage and a microorganism number-measuring AC voltage to the pair of comb-like electrodes of the measurement electrode in the first liquid during a measurement operation thereby converting the first liquid into a second liquid, the second liquid having been exposed to the microorganism collecting AC voltage and the microorganism number-measuring AC voltage;
the power supply also supplying a disconnection voltage to the pair of comb-like electrodes of the measurement electrode in the second liquid after the measurement operation, wherein the disconnection voltage causes the pair of comb-like electrodes to heat up and to be peeled from the substrate by the heat; and resulting in a visually confirmable burned out comb-like electrode.

2. The microorganism number-measuring apparatus according to claim 1, wherein:

the container includes a measurement space, the measurement electrode includes a portion disposed in the measurement space, the measurement electrode configured to be used in the measurement operation and to burn out, the portion is configured to contact the microorganisms in the measurement operation, and the burn out of the electrode includes burning out the portion disposed in the measurement space.

3. The microorganism number-measuring apparatus of claim 1 wherein the disconnection voltage is an AC voltage having a non-commercial frequency lower than a commercial frequency, wherein the commercial frequency is 50-60 Hz.

4. The microorganism number-measuring apparatus of claim 1 wherein the disconnection voltage is a DC voltage.

5. The microorganism number-measuring apparatus of claim 4 wherein the microorganism collecting AC voltage has a frequency higher than the commercial frequency, wherein the commercial frequency is 50-60 Hz.

6. The microorganism number-measuring apparatus of claim 5 wherein the microorganism number-measuring AC voltage has a frequency higher than the commercial frequency.

7. The microorganism number-measuring apparatus of claim 4 wherein the microorganism number-measuring AC voltage has a frequency higher than the commercial frequency, wherein the commercial frequency is 50-60 Hz.

8. A microorganism number-measuring method using the microorganism number-measuring apparatus of claim 1, the method comprising:

generating a stream in the first liquid;

controlling the power supply to supply a microorganism-collecting voltage and a microorganism number-measuring voltage to a measurement electrode during a measurement operation of the measurement electrode; and controlling the power supply to burn out the measurement electrode immersed in the second liquid while generating the stream to peel the measurement electrode off from the substrate after the measurement operation of the measurement electrode.

* * * * *